(12) United States Patent
Miyazaki et al.

(10) Patent No.: US 9,622,769 B2
(45) Date of Patent: Apr. 18, 2017

(54) FLUID EJECTION DEVICE

(71) Applicant: SEIKO EPSON CORPORATION, Tokyo (JP)

(72) Inventors: Koichiro Miyazaki, Ina (JP); Masaki Gomi, Hino (JP); Takahiro Matsuzaki, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 232 days.

(21) Appl. No.: 14/681,000

(22) Filed: Apr. 7, 2015

(65) Prior Publication Data

US 2015/0282830 A1 Oct. 8, 2015

(30) Foreign Application Priority Data

Apr. 8, 2014 (JP) ................................. 2014-079189

(51) Int. Cl.
*A61B 17/3203* (2006.01)
*A61B 17/00* (2006.01)

(52) U.S. Cl.
CPC ..... *A61B 17/3203* (2013.01); *A61B 2017/00017* (2013.01); *A61B 2017/00154* (2013.01)

(58) Field of Classification Search
CPC ...... A61B 17/3203; A61B 2017/00154; A61B 2017/00017
USPC .......................................... 83/177; 606/167
See application file for complete search history.

(56) References Cited

U.S. PATENT DOCUMENTS

| 6,135,977 A | 10/2000 | Drasler et al. |
| 2008/0086077 A1 | 4/2008 | Seto et al. |
| 2013/0213200 A1* | 8/2013 | Cooper .................. B26F 3/004 83/23 |
| 2013/0310862 A1 | 11/2013 | Seto et al. |

FOREIGN PATENT DOCUMENTS

| JP | 2008-082202 A | 4/2008 |
| WO | 2010/148125 A1 | 12/2010 |
| WO | 2013/130895 A1 | 9/2013 |

OTHER PUBLICATIONS

Extended European Search Report dated May 27, 2015 as received in Application No. 15 16 2374.

* cited by examiner

*Primary Examiner* — Julian W Woo
(74) *Attorney, Agent, or Firm* — Maschoff Brennan

(57) ABSTRACT

A fluid ejection device includes a fluid ejection unit including a plurality of nozzles and configured to eject fluid from at least any one of the nozzles in a pulse-like manner according to a drive signal, a fluid supplying unit configured to supply the fluid to the fluid ejection unit, an ejecting-instruction input unit configured to receive an ejecting instruction input, a mode-selection input unit configured to receive an input of selection information for selecting any one of a first mode for ejecting the fluid using a first nozzle unit including at least one nozzle and a second mode for ejecting the fluid using a second nozzle unit including at least one nozzle, and a fluid-ejecting control unit configured to output, when receiving the ejecting instruction input, according to the selection information, the drive signal such that the fluid is ejected from the first nozzle unit or second nozzle unit.

8 Claims, 9 Drawing Sheets

| | MODE A | MODE B | MODE C |
|---|---|---|---|
| CROSS SECTIONAL AREA OF FIRST FLUID-EJECTING OPENING SECTION (S1) | 212a ● | 212a ● | 212a ○ |
| CROSS SECTIONAL AREA OF SECOND FLUID-EJECTING OPENING SECTION (S2) | 212b ○ | 212b ● | 212b ● |
| CROSS SECTIONAL AREA OF THIRD FLUID-EJECTING OPENING SECTION (S3) | 212c ○ | 212c ● | 212c ● |
| CROSS SECTIONAL AREA OF FOURTH FLUID-EJECTING OPENING SECTION (S4) | 212d ○ | 212d ● | 212d ● |
| CROSS SECTIONAL AREA OF FIFTH FLUID-EJECTING OPENING SECTION (S5) | 212e ○ | 212e ● | 212e ● |
| TOTAL AREA OF CROSS SECTIONS OF FLUID-EJECTING OPENING SECTIONS | SA=S1 | SB= S1+S2+S3+S4+S5 | SC= S2+S3+S4+S5 |

FLUID EJECTION DEVICE

This application claims the benefit of Japanese Patent Application No. 2014-079189 filed on Apr. 8, 2014. The content of aforementioned application is incorporated herein by reference in its entirety.

BACKGROUND

1. Technical Field

The present invention relates to a fluid ejection device.

2. Related Art

There is known a technique for ejecting fluid in a pulse-like manner to perform incision, excision, or the like of a target object. For example, in the medical field, as a surgical instrument for incising or excising a biological tissue, there is proposed a fluid ejection device including a pulsed flow generating unit that ejects fluid in a pulse-like manner, a fluid supplying unit that supplies the fluid to the pulsed flow generating unit, and a fluid supply path that connects the fluid supplying unit and the pulsed flow generating unit (see, for example, JP-A-2008-082202 (Patent Literature 1)).

Such a fluid ejection device can efficiently incise the biological tissue by ejecting the fluid in a pulse-like manner from a single nozzle included in the pulsed flow generating unit.

However, during a surgical operation, it is sometimes desired to not only incise the biological tissue but also eject the fluid to a region having a certain degree of spread and efficiently crush the biological tissue, for example, when the biological tissue is excised. In such a case, when the fluid is only ejected from the single nozzle, it is likely that work efficiency is deteriorated because, for example, a long time is required for work.

Therefore, there is a demand for a technique for making it possible to more efficiently perform the crushing of the biological tissue.

SUMMARY

A fluid ejection device according to an aspect of the invention includes: a fluid ejection unit including a plurality of nozzles for ejecting fluid and configured to eject the fluid from at least any one of the nozzles in a pulse-like manner according to a drive signal; a fluid supplying unit configured to supply the fluid to the fluid ejection unit; an ejecting-instruction input unit configured to receive an ejecting instruction input for ejecting the fluid from the fluid ejection unit; a mode-selection input unit configured to receive an input of selection information for selecting, when the fluid is ejected from the fluid ejection unit, any one of a first mode for ejecting the fluid using a first nozzle unit including at least one of the plurality of nozzles and a second mode for ejecting the fluid using a second nozzle unit including at least one of the plurality of nozzles; and a fluid-ejecting control unit configured to output, when receiving the ejecting instruction input, according to the selection information, the drive signal to the fluid ejection unit such that the fluid is ejected from the first nozzle unit or the second nozzle unit. A total area of cross sections of ejection ports of the nozzles belonging to the second nozzle unit is larger than a total area of cross sections of ejection ports of the nozzles belonging to the first nozzle unit.

Other features of the invention will be made apparent by the description of this specification and the accompanying drawings.

BRIEF DESCRIPTION OF THE DRAWINGS

The invention will be described with reference to the accompanying drawings, wherein like numbers reference like elements.

FIG. 6 is a diagram showing an example of ejecting patterns in modes selectable by a pulsation-generating-unit changeover switch according to the embodiment of the invention.

DESCRIPTION OF EXEMPLARY EMBODIMENTS

Overview

Figure 1:
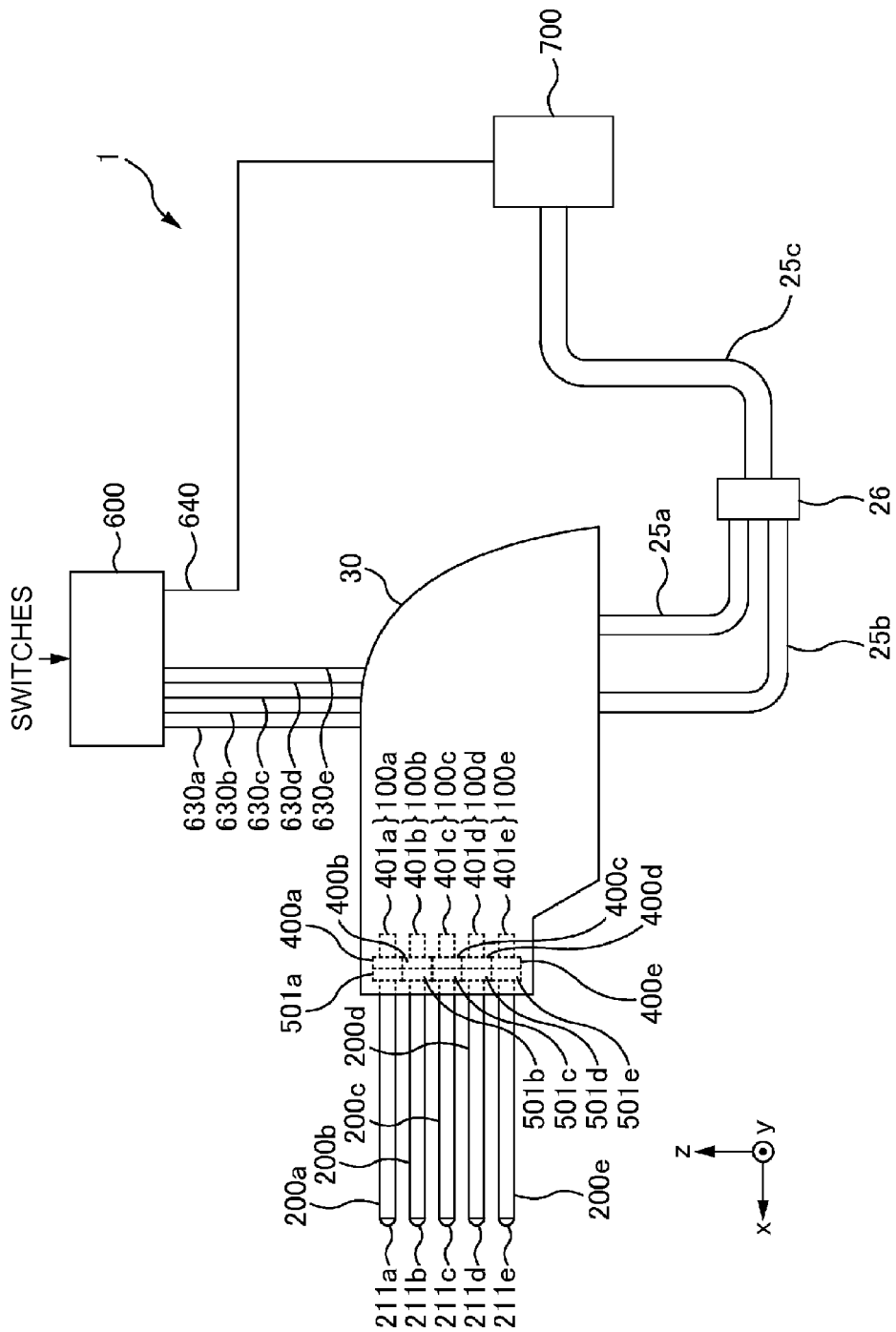
FIG. 1 is a block diagram showing an example of the overall configuration of a fluid ejection device according to an embodiment of the invention.

At least matters described below are made apparent by the description of this specification and the drawings.

A fluid ejection device includes: a fluid ejection unit including a plurality of nozzles for ejecting fluid and configured to eject the fluid from at least any one of the nozzles in a pulse-like manner according to a drive signal; a fluid supplying unit configured to supply the fluid to the fluid ejection unit; an ejecting-instruction input unit configured to receive an ejecting instruction input for ejecting the fluid from the fluid ejection unit; a mode-selection input unit configured to receive an input of selection information for selecting, when the fluid is ejected from the fluid ejection unit, any one of a first mode for ejecting the fluid using a first nozzle unit including at least one of the plurality of nozzles and a second mode for ejecting the fluid using a second nozzle unit including at least one of the plurality of nozzles; and a fluid-ejecting control unit configured to output, when receiving the ejecting instruction input, according to the selection information, the drive signal to the fluid ejection unit such that the fluid is ejected from the first nozzle unit or the second nozzle unit. A total area of cross sections of ejection ports of the nozzles belonging to the second nozzle unit is larger than a total area of cross sections of ejection ports of the nozzles belonging to the first nozzle unit.

With such a fluid ejection device, it is possible to efficiently perform incision of a biological tissue by ejecting the fluid from the first nozzle unit having the smaller total areas of the ejection ports. It is possible to efficiently perform crushing of the biological tissue by ejecting the fluid from the second nozzle unit having the larger total area of the ejection ports.

It is preferable that the nozzles belonging to the first nozzle unit also belong to the second nozzle unit.

With such a fluid ejection device, when the fluid is ejected from the second nozzle unit, the total area of the ejection ports of the second nozzle unit further increases by the areas of the ejection ports of the nozzles also belonging to the first nozzle unit. Therefore, it is possible to more effectively perform the crushing of the biological tissue.

On the other hand, it is preferable that the nozzles belonging to the first nozzle unit do not belong to the second nozzle unit.

With such a fluid ejection device, it is possible to optimize the first nozzle unit and the second nozzle unit according to uses of the respective nozzle units. It is possible to optimize, for example, the sectional areas and the lengths of the nozzles respectively in the first nozzle unit and the second nozzle unit.

It is preferable that, when the fluid ejection unit ejects the fluid, if the first mode is selected, the fluid supplying unit supplies a first predetermined amount of the fluid to the fluid ejection unit per a predetermined time and, if the second mode is selected, the fluid supplying unit supplies a second predetermined amount of the fluid to the fluid ejection unit per the predetermined time.

With such a fluid ejection device, when the modes are selected, it is possible to eject an appropriate amount of the fluid when the fluid is ejected from the first nozzle unit and when the fluid is ejected from the second nozzle unit.

It is preferable that the second predetermined amount is larger than the first predetermined amount.

With such a fluid ejection device, it is possible to further increase an amount of the fluid ejected from the second nozzle unit having the larger total area of the cross sections of the ejection ports. Therefore, it is possible to efficiently perform the crushing of the biological tissue.

It is preferable that, if the first mode is selected, the fluid ejection unit ejects the fluid from the nozzles belonging to the first nozzle unit at first ejecting strength and, if the second mode is selected, the fluid ejection unit ejects the fluid from the nozzles belonging to the second nozzle unit at second ejecting strength.

With such a fluid ejection device, when the modes are selected, it is possible to eject the fluid at appropriate ejecting strength irrespective of the modes.

It is preferable that the second ejecting strength is higher than the first ejecting strength.

With such a fluid ejection device, when the fluid ejected using the second nozzle unit having the larger total area of the cross sections of the ejection ports, the fluid can be ejected at higher ejecting strength. Therefore, it is possible to more efficiently perform the crushing of the biological tissue.

It is preferable that a singularity of the nozzle belongs to the first nozzle unit, and the nozzles belonging to the second nozzle unit include all the nozzles other than the nozzle belonging to the first nozzle unit.

With such a fluid ejection device, when a biological tissue is incised, since fluid can be eject in a straight line from a single nozzle, it is possible to accurately eject the fluid to a position to be incised. Further, when the biological tissue is crushed, since the fluid can be ejected to a wide range from the plurality of nozzles, it is possible to efficiently crush the biological tissue to be crushed.

Overall Configuration

An embodiment of the invention is explained below with reference to the drawings. A fluid ejection device according to this embodiment is adoptable for cleaning, cutting, and the like of fine objects, structures, biological tissues, and the like. In the embodiment explained below, a fluid ejection device suitable for a surgical knife for incising or excising a biological tissue is illustrated. Therefore, fluid used in the fluid ejection device according to this embodiment is water, saline, predetermined chemical, or the like. Note that, drawings referred to in the following explanation are schematic diagrams in which, for convenience of illustration, longitudinal and lateral scales of members and portions are different from actual scales.

FIG. 1 is a schematic explanatory diagram showing a fluid ejection device 1 functioning as a surgical knife according to this embodiment. The fluid ejection device 1 according to this embodiment includes a driving control unit (a fluid-ejecting control unit) 600, a hand piece (a fluid ejection unit) 30, a pump (a fluid supplying unit) 700, a first connection tube 25a, a second connection tube 25b, a third connection tube 25c, and a channel switching valve 26.

The driving control unit 600 performs control of the fluid ejection device 1 in cooperation with the pump 700.

The pump 700 supplies the fluid to the hand piece 30 via the first connection tube 25a, the second connection tube 25b, and the third connection tube 25c.

The hand piece 30 ejects the fluid, which is supplied from the pump 700, in a pulse-like manner.

As an example, the hand piece 30 includes five pulsation generators 100, i.e., a first pulsation generator 100a, a second pulsation generator 100b, a third pulsation generator 100c, a fourth pulsation generator 100d, and a fifth pulsation generator 100e.

Note that, the functions and the structures of the first pulsation generator 100a, the second pulsation generator 100b, the third pulsation generator 100c, the fourth pulsation generator 100d, and the fifth pulsation generator 100e are the same. Therefore, for simplification of explanation, the first pulsation generator 100a, the second pulsation generator 100b, the third pulsation generator 100c, the fourth pulsation generator 100d, and the fifth pulsation generator 100e are collectively referred to as pulsation generators 100 as appropriate and explained except when it is particularly necessary to distinguish and explain the pulsation generators. The other components are also collectively explained as appropriate when the functions and the structures of the components are the same.

The detailed configuration of the pulsation generators 100 is explained below. The pulsation generators 100 according to this embodiment include thin pipe-like fluid ejecting pipes 200 functioning as channels when the fluid is ejected and distal-end opening sections 211 with a reduced channel diameter attached to the distal end portions of the fluid ejecting pipes 200.

The pulsation generators 100 include fluid chambers 501 in which the fluid supplied from the pump 700 is stored, diaphragms 400 that change the volume of the fluid chambers 501, and piezoelectric elements 401 that vibrate the diaphragms 400.

The pulsation generators 100 drive the piezoelectric elements 401 with a drive signal output from the driving control units 600 and change the volume of the fluid chambers 500 to apply pressure to the fluid in a pulse-like manner and convert the fluid into a pulsed flow, and eject the fluid in a pulse-like manner at high speed through the fluid ejecting pipes 200 and the distal-end opening portions 211.

Note that coordinate axes shown in FIG. 1 are shown in order to explain the arrangement of the pulsation generators 100 included in the hand piece 30. In this embodiment, when the hand piece 30 is fixed such that the fluid is ejected in the horizontal direction from the distal-end opening sections 211 provided at the distal ends of the fluid ejecting pipes 200, a direction in which the fluid is ejected is plotted on an x axis, the vertical upper direction is plotted on a z axis, and a direction on the left side with respect to the direction of the x axis is plotted on a y axis. The same applies in the other figures referred to below.

In FIG. 1, the hand piece 30 is shown such that, when the x-axis direction is represented as an ejecting direction, the five pulsation generators 100 are arranged side by side in the z-axis direction, which is a direction crossing the ejecting direction.

The first connection tube 25a, the second connection tube 25b, and the third connection tube 25c configure a channel of the fluid from the pump 700 to the hand piece 30.

In the following explanation, a channel of the fluid configured by the third connection tube 25c and the first connection tube 25a is also referred to as first channel. A channel of the fluid configured by the third connection tube 25c and the second connection tube 25b is also referred to as second channel.

The first connection tube 25a, the second connection tube 25b, and the third connection tube 25c are also collectively referred to as connection tubes 25 as appropriate.

The channel switching valve 26 is a valve capable of individually independently performing switching of communication and closing of the first channel configured by the first connection tube 25a and the third connection tube 25c and switching of communication and closing of the second channel configured by the second connection tube 25b and the third connection tube 25c.

Therefore, by variously controlling the channel switching valve 26, it is possible to supply the fluid, which is supplied from the pump 700, to the hand piece 30 via only the first channel, supply the fluid to the hand piece 30 via only the second channel, and supply the fluid to the hand piece 30 via both of the first channel and the second channel.

Note that the hand piece 30 according to this embodiment is configured to eject the fluid, which is supplied via the first channel, from the first pulsation generator 100a and eject the fluid, which is supplied via the second cannel, from the second pulsation generator 100b, the third pulsation generator 100c, the fourth pulsation generator 100d, and the fifth pulsation generator 100e.

As explained in detail below, the first pulsation generator 100a is used when a surgeon who performs a surgical operation using the hand piece 30 incises a biological tissue. On the other hand, the second to fifth pulsation generators 100b to 100e are used when the surgeon crushes the biological tissue. When the surgeon crushes the biological tissue, it is possible to use the first to the fifth pulsation generators 110a to 100e.

The driving control unit 600 and the pulsation generators 100 are connected by control cables 630. Specifically, the driving control unit 600 and the first pulsation generator 100a are connected by a first connection cable 630a, the driving control unit 600 and the second pulsation generator 100b are connected by a second control cable 630b, the driving control unit 600 and the third pulsation generator 100c are connected by a third control cable 630c, the driving control unit 600 and the fourth pulsation generator 100d are connected by a fourth control cable 630d, and the driving control unit 600 and the fifth pulsation generator 100e are connected by a fifth control cable 630e.

When ejecting the fluid from the first pulsation generator 100a in a pulse-like manner, the driving control unit 600 transmits a drive signal (a first drive signal) to the first pulsation generator 100a via the first control cable 630a. When the first drive signal is input, the first pulsation generator 100a drives the first piezoelectric element 401a and changes the volume of the first fluid chamber 501a to apply pressure to the fluid in a pulse-like manner and convert the fluid into a pulsed flow, and ejects the fluid in a pulse-like manner at high speed through a first fluid ejecting pipe 200a and a first distal-end opening section 211a. The same applies to the second to fifth pulsation generators 100b to 100e.

The driving control unit 600 and the pump 700 are connected by a communication cable 640. The driving control unit 600 and the pump 700 exchange various commands and data each other according to a predetermined communication protocol such as a CAN (Controller Area Network).

The driving control unit 600 receives inputs of signals from various switches operated by the surgeon or the like who performs a surgical operation using the hand piece 30. The driving control unit 600 controls the pump 700 and the pulsation generators 100 via the control cables 630 and the communication cable 640.

As the switches connected to the driving control unit 600, there are, for example, a pulsation-generating-unit start switch (an ejecting-instruction input unit) 625, an ejecting-strength changeover switch 627, a flushing switch 628, and a pulsation-generating-unit changeover switch (a mode-selection input unit) 629 (not shown in the figure).

The pulsation-generating-unit changeover switch 629 is a switch for receiving an input of selection information for selecting from which pulsation generator 100 among the plurality of pulsation generators 100 in the hand piece 30 the fluid is ejected.

The surgeon can select, by operating the pulsation-generating-unit changeover switch 629, any one of a first mode for ejecting the fluid using a first nozzle unit including at last one of the plurality of pulsation generators 100 and a second mode for ejecting the fluid using a second nozzle unit including at least one of the plurality of pulsation generators 100.

Note that, in this embodiment, in the following explanation, the first mode is equivalent to a mode A and the second mode is equivalent to a mode B or a mode C.

The mode A is a mode for ejecting the fluid from only the first pulsation generator 100a. The mode B is a mode for ejecting the fluid from all of the first to the fifth pulsation generators 100a to 100e. The mode C is a mode for ejecting the fluid from the second to fifth pulsation generators 100b to 100e.

The driving control unit 600 outputs a drive signal to the control cable 630 connected to the pulsation generator 100 used in the selected mode. The driving control unit 600 switches the channel switching valve 26 such that the fluid is supplied to the pulsation generator 100 used in the selected mode.

Note that the mode A is selected when a biological tissue is incised. On the other hand, the mode B and the mode C are selected when the biological tissue is crushed.

The pulsation-generating-unit start switch 625 is a switch for switching presence or absence of ejecting of the fluid from the hand piece 30. When the pulsation-generating-unit start switch 625 is operated by the surgeon who performs a surgical operation using the hand piece 30, the driving control unit 600 executes, in cooperation with the pump 700, control for ejecting the fluid or stopping the ejecting of the fluid from the pulsation generator 100 used in the mode selected by the pulsation-generating-unit changeover switch 629. The pulsation-generating-unit start switch 625 can take a form of a footswitch operated by the foot of the surgeon or can take a form of being disposed integrally with the hand piece 30, which is gripped by the surgeon, and operated by the hand and the fingers of the surgeon.

The ejecting-strength changeover switch 627 is a switch for changing ejecting strength of the fluid ejected from the pulsation generators 100. When the ejecting-strength-changeover switch 627 is operated, the driving control unit 600 applies control for increasing or reducing the ejecting strength of the fluid to the pulsation generators 100 and the pump 700.

For example, when ejecting the fluid from the pulsation generator 100, the driving control unit 600 outputs a drive signal corresponding to ejecting strength set by the ejecting-strength changeover switch 627 to the pulsation generator 100. Specifically, the driving control unit 600 increases the frequency of the driving voltage when the ejecting strength is increased and reduces the frequency of the driving voltage when the ejecting strength is reduced. Alternatively, the driving control unit 600 may increase the driving voltage when the ejecting strength is increased and reduce the driving voltage when the ejecting strength is reduced.

When supplying the fluid to the pulsation generator 100, the pump 700 controls the pressure of the fluid in the pump 700 to be pressure corresponding to the ejecting strength set by the ejecting-strength changeover switch 627. For example, the pump 700 increases the pressure of the fluid when the ejecting strength is increased and reduces the pressure of the fluid when the ejecting strength is reduced.

Note that the ejecting-strength changeover switch 627 may be a switch configured to be capable of alternatively selecting ejecting strength out of a plurality of ejecting strengths determined beforehand or may be a switch configured to be capable of continuously changing the ejecting strength from an upper limit value to a lower limit value.

The ejecting strength set by the ejecting-strength-changeover switch 627 is determined using some physical quantity (e.g., pressure applied to an ejecting target object, an ejecting amount per a predetermined time, or flow velocity) that could be an index of the ejecting strength. However, the ejecting strength can be any physical quantity.

Note that the flushing switch 628 is explained below.

In this embodiment, the pulsed flow means flowing of the fluid that flows in a fixed direction and involves cyclic or irregular fluctuation of a flow rate or flow velocity of the fluid. The pulsed flow also includes an intermittent flow that repeats flowing and stop of the fluid. However, since the flow rate or the flow velocity of the fluid only has to cyclically or irregularly fluctuates, the pulsed flow does not always need to be the intermittent flow.

Similarly, ejecting the fluid in a pulse-like manner means ejecting of the fluid, the flow rate or the flow velocity of which cyclically or irregularly fluctuates. Examples of the pulse-like ejecting include intermittent ejecting that repeats ejecting and non-ejecting of the fluid. However, since the flow rate or the flow velocity of the ejected fluid only has to cyclically or irregularly fluctuates, the ejecting of the fluid does not always need to be intermittent ejecting.

When the pulsation generators 100 stop the driving, that is, when the pulsation generators 100 do not change the volume of the fluid chambers 501, the fluid supplied from the pumps 700 functioning as fluid supplying units at predetermined pressure continuously flows out from the distal-end opening portions 211 through the fluid chambers 501.

Pump

An overview of the configuration and the operation of the pump 700 according to this embodiment is explained with reference to FIG. 2.

The pump 700 according to this embodiment includes a pump control unit 710, a slider 720, a motor 730, a linear guide 740, and a pinch valve 750. The pump 700 includes a fluid-container attaching unit 770 for detachably attaching a fluid container 760 that stores the fluid. The fluid-container attaching unit 770 is formed to hold the fluid container 760 in a specified position when the fluid container 760 is attached.

As explained in detail below, a slider release switch 780, a slider set switch 781, a fluid-feed ready switch 782, a priming switch 783, and a pinch valve switch 785 are connected to the pump control unit 710 (not shown in the figure).

In this embodiment, as an example, the fluid container 760 is configured as an injection cylinder including a syringe 761 and a plunger 762.

In the fluid container 760, an opening section 764 having a projected cylindrical shape is formed at the distal end portion of the syringe 761. When the fluid container 760 is attached to the fluid-container attaching unit 770, an end portion of the connection tube 25 (the third connection tube 25c) is fit in the opening section 764 to form a channel of the fluid from the inside of the syringe 761 to the connection tube 25.

The pinch valve 750 is a valve that is provided on a route of the connection tube 25 (the third connection tube 25c) and opens and closes a channel of the fluid between the fluid container 760 and the pulsation generator 100.

Opening and closing of the pinch valve 750 is performed by the control unit 710. When the pump control unit 710 opens the pinch valve 750, the fluid container 760 and the pulsation generator 100 communicate with each other through the channel. When the pump control unit 710 closes the pinch valve 750, the channel between the fluid container 760 and the pulsation generator 100 is blocked.

After the fluid container 760 is attached to the fluid-container attaching unit 770, when the plunger 762 of the fluid container 760 is moved in a direction for pushing the plunger 762 into the syringe 761 (hereinafter also referred to as push-in direction) in a state in which the pinch valve 750 is opened, the volume of a space (hereinafter also referred to as fluid storing unit 765) surrounded by an end face of a gasket 763, which is made of resin such as rubber having elasticity, attached to the distal end on the push-in direction side of the plunger 762 and the inner wall of the syringe 761 decreases. The fluid filled in the fluid storing unit 765 is ejected from the opening section 764 at the distal end portion of the syringe 761. The fluid ejected from the opening section 764 is filled in the connection tube 25 and supplied to the pulsation generator 100.

On the other hand, after the fluid container 760 is attached to the fluid-container attaching unit 770, when the plunger 762 of the fluid container 760 is moved in the push-in direction in a state in which the pinch valve 750 is closed, the volume of the fluid storing unit 765 surrounded by the gasket 763 attached to the distal end of the plunger 762 and the inner wall of the syringe 761 decreases. The pressure of the fluid filled in the fluid storing unit 765 can be increased.

The movement of the plunger 762 is performed by the pump control unit 710 moving the slider 720 along a direction in which the plunger 762 slides when the fluid container 760 is attached to the fluid-container attaching unit 770 (the push-in direction and the opposite direction of the push-in direction).

Specifically, the slider 720 is attached to the linear guide 740 to engage a pedestal section 721 of the slider 720 to a rail (not shown in the figure) linearly formed in the linear guide 740 along the sliding direction of the plunger 762. The linear guide 740 moves the pedestal section 721 of the slider 720 along the rail using power transmitted from the motor 730 driven by the pump control unit 710, whereby the slider 720 moves in the sliding direction of the plunger 762.

Figure 2:
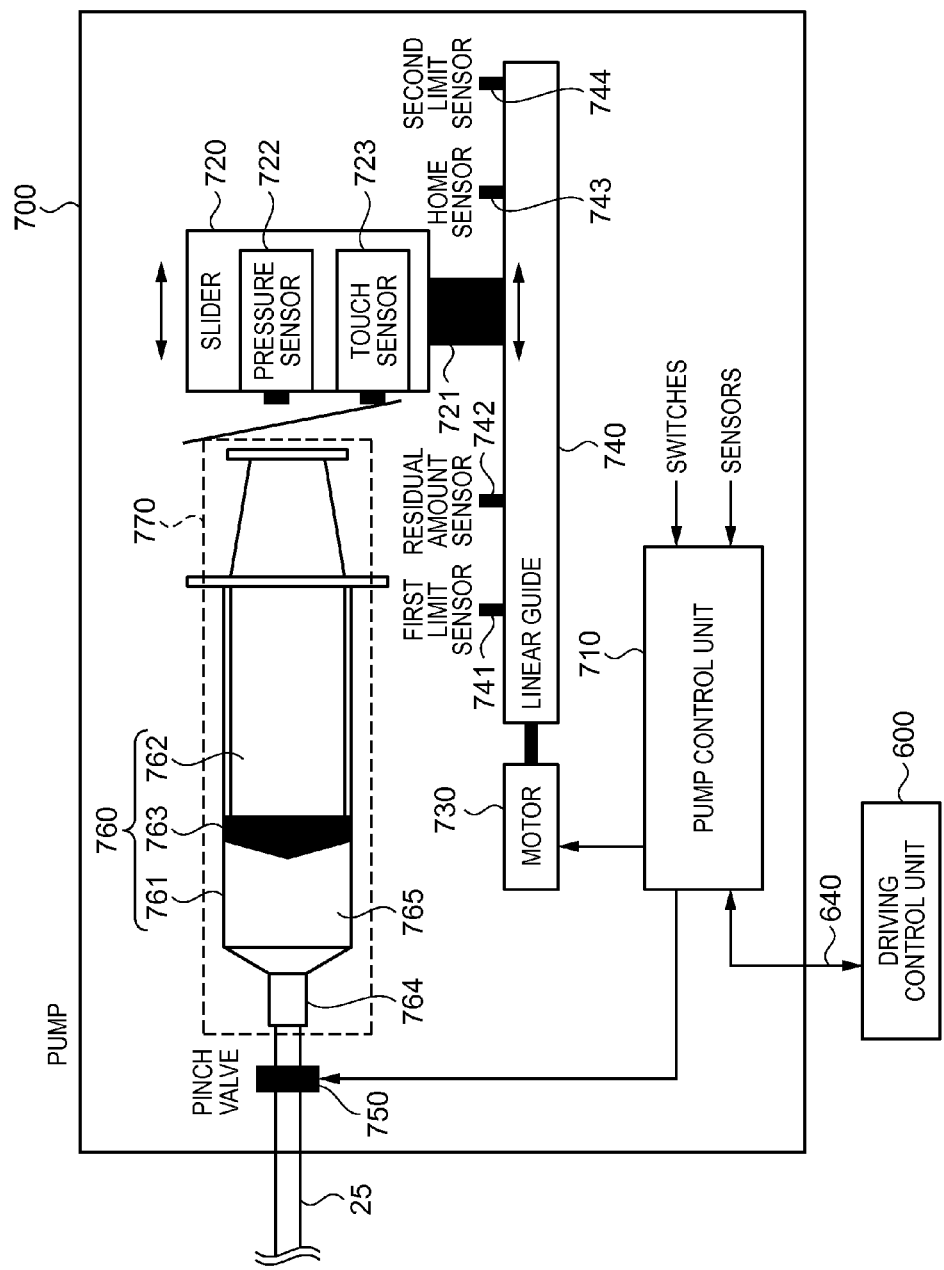
FIG. 2 is a block diagram showing the configuration of a pump according to the embodiment of the invention.

As shown in FIG. 2, a first limit sensor 741, a residual amount sensor 742, a home sensor 743, and a second limit sensor 744 are provided along the rail of the linear guide 740.

All of the first limit sensor 741, the residual amount sensor 742, the home sensor 743, and the second limit sensor 744 are sensors that detect the position of the slider 720 that moves on the rail of the linear guide 740. Signals detected by the sensors are input to the pump control unit 710.

The home sensor 743 is a sensor used for determining an initial position (hereinafter also referred to as home position) of the slider 720 on the linear guide 740. The home position is a position where the slider 720 is held when work such as attachment and replacement of the fluid container 760 is performed.

The residual amount sensor 742 is a sensor for detecting the position of the slider 720 (hereinafter also referred to as residual amount position) where the residual amount of the fluid in the fluid container 760 is equal to or smaller than a predetermined value when the slider 720 moves in the push-in direction of the plunger 762 from the home position. When the slider 720 moves to the residual amount position where the residual amount sensor 742 is provided, predetermined an alarm is output to the operator (the surgeon or an assistant). The operator determines to perform work for replacing the fluid container 760 currently in use with a new fluid container 760 at appropriate timing. Alternatively, when an auxiliary second pump 700b having the same configuration as the pump 700 (the first pump 700a) is prepared, switching work is performed to supply the fluid to the pulsation generator 100 from the auxiliary second pump 700b.

The first limit sensor 741 indicates a limit position (hereinafter also referred to as first limit position) in a movable range of the slider 720 moving in the push-in direction of the plunger 762 from the home position. When the slider 720 moves to the first limit position where the first limit sensor 741 is provided, the residual amount of the fluid in the fluid container 760 is smaller than the residual amount at the time when the slider 720 is in the residual amount position. A predetermined alarm is output to the operator. In this case as well, the work for replacing the fluid container 760 currently in use with the new fluid container 760 or the switching work to the auxiliary second pump 700b is performed.

On the other hand, the second limit sensor 744 indicates a limit position (hereinafter also referred to as second limit position) of the movable range of the slider 720 moving in the opposite direction of the push-in direction of the plunger 762 from the home position. The predetermined alarm is also output when the slider 720 moves to the second limit position where the second limit sensor 744 is provided.

A touch sensor 723 and a pressure sensor (a pressure detecting unit) 722 are attached to the slider 720.

The touch sensor 723 is a sensor for detecting whether the slider 720 is in contact with the plunger 762 of the fluid container 760.

The pressure sensor 722 is a sensor that detects the pressure of the fluid in the fluid storing unit 765 formed by the inner wall of the syringe 761 and the gasket 763, that is, the pressure of the slider 720 in pressing the fluid storing unit 765 and outputs a signal (a detection signal) of a level (e.g., a voltage, an electric current, or a frequency) corresponding to the pressure.

When the slider 720 is moved in the push-in direction in a state in which the pinch valve 750 is closed, after the slider 720 comes into contact with the plunger 762, the pressure of the fluid in the fluid storing unit 765 rises as a push-in amount of the slider 720 is increased.

On the other hand, when the slider 720 is moved in the push-in direction in a state in which the pinch valve 750 is opened, even after the slider 720 comes into contact with the plunger 762, the fluid in the fluid storing unit 765 flows out from the distal-end opening portion 211 of the pulsation generator 100 through the connection tube 25. Therefore, the pressure of the fluid in the fluid storing unit 765 rises to a certain degree but does not rise even if the slider 720 is further moved in the push-in direction.

Note that signals from the touch sensor 723 and the pressure sensor 722 are input to the pump control unit 710.

In the following explanation, the slider 720, the motor 730, and the linear guide 740 are sometimes referred to as fluid pressing unit 731. The fluid pressing unit 731 presses the fluid storing unit 765 and causes the fluid to flow out from the opening section 764 of the fluid container 760.

A preparation operation for attaching the fluid container 760, in which the fluid is filled, to the fluid-container attaching unit 770 anew, supplying the fluid in the fluid container 760 to the pulsation generator 100, and enabling the fluid to be ejected from the pulsation generator 100 in a pulse-like manner is explained.

The preparation operation is an operation performed for changing the fluid in the channel to a predetermined state such that the fluid is ejected from the pulsation generator 100 at appropriate strength.

The preparation operation includes various kinds of processing such as preliminary pressurization, priming processing, and flushing processing. The pump control unit 710 and the driving control unit 600 can execute the preparation operation in various combinations of these kinds of processing according to a state of the fluid ejection device 1.

First, the operator operates the slider release switch 780 to input an ON signal of the slider release switch 780 to the pump control unit 710. Then, the pump control unit 710 moves the slider 720 to the home position.

The operator attaches the fluid container 760, which is connected to the connection tube 25 beforehand, to the fluid-container attaching unit 770. Note that the fluid is already filled in the syringe 761 of the fluid container 760.

After setting the connection tube 25 in the pinch valve 750, when the operator operates the pinch valve switch 785 to input an ON signal of the pinch valve switch 785 to the pump control unit 710, the pump control unit 710 closes the pinch valve 750.

Subsequently, the operator operates the slider set switch 781 to input an ON signal of the slider set switch 781 to the pump control unit 710. Then, the pump control unit 710 moves the slider 720 in the push-in direction and starts control such that the pressure of the fluid stored in the fluid storing unit 765 in the fluid container 760 is within a specified range (hereinafter also referred to as rough window) with respect to a predetermined target pressure value.

As explained above, the preliminary pressurization is processing for setting the pressure of the fluid stored in the fluid storing unit 765 within the specified range.

Thereafter, when the fluid-feed ready switch 782 is pressed by the operator, an ON signal of the fluid-feed ready switch 782 is input to the pump control unit 710. When the pressure of the fluid in the fluid storing unit 765 is in the rough window, the pump control unit 710 changes to a fluid feedable state in which feeding of the fluid from the pump 700 to the pulsation generator 100 is permitted.

In the fluid feedable state of the pump control unit 710, when an ON signal of the priming switch 783 is input to the pump control unit 710 by the operation by the operator, the pump control unit 710 starts the priming processing. The priming processing is processing for causing the fluid in the fluid container 760 to reach a fluid-ejecting opening section 212 of the pulsation generator 100 via the connection tube 25 and fill a channel from the fluid container 760 to the fluid-ejecting opening section 212 with the fluid.

When the priming processing is started, the pump control unit 710 opens the pinch valve 750 and starts movement in the push-in direction of the slider 720 at timing simultaneous or substantially simultaneous with the opening of the pinch valve 750 (e.g., with a time difference of about several milliseconds to several tens milliseconds). The driving control unit 600 controls the channel switching valve 26 to supply the fluid from the pump 700 to the hand piece 30 through both of the first channel and the second channel.

The movement of the slider 720 is performed at predetermined speed at which a delivery amount per unit time of the fluid from the fluid container 760 is fixed. The priming processing is performed until a predetermined time equal to or longer than time required by the fluid in the fluid container 760 to reach the fluid-ejecting opening section (an ejection port) 212 of the pulsation generator 100 elapses (or the slider 720 moves a predetermined distance sufficient for the fluid in the fluid container 760 to reach the fluid-ejecting opening section 212 of the pulsation generator 100) or until the operator operates the priming switch 783 to input an OFF signal.

Consequently, a predetermined amount of the fluid in the fluid storing unit 765 is delivered from the pump 700 at predetermined flow velocity (an ejection amount of the fluid per unit time) and fills the inside of the connection tube 25 from the pinch valve 750 to the pulsation generator 100 and also fills the fluid chamber 501 of the pulsation generator 100, the fluid ejecting pipe 200, and the like. Note that the air present in the connection tube 25 and the pulsation generator 100 before the start of the priming processing is emitted to the atmosphere from the distal-end opening portion 211 of the pulsation generator 100 as the fluid flows into the connection tube 25 and the pulsation generator 100.

Note that the predetermined speed, the predetermined distance, or the predetermined time for moving the slider 720 in the priming processing is stored in the pump control unit 710 beforehand.

In this way, the priming processing is completed.

Subsequently, when an ON signal of the flushing switch 628 is input to the driving control unit 600 by the operation by the operator, the driving control unit 600 and the pump control unit 710 start degassing processing.

The degassing processing is processing for discharging air bubbles remaining in the connection tube 25 and the pulsation generator 100 from the distal-end opening portion 211 of the pulsation generator 100 and removing the air bubbles from the channel.

In the degassing processing, in a state in which the pinch valve 750 is opened, the pump control unit 710 moves the slider 720 in the push-in direction at predetermined speed for fixing a delivery amount per unit time of the fluid from the fluid container 760, that is, speed for setting a flow rate of the fluid flowing in a predetermined time in the channel to a predetermined amount and supplies the fluid to the pulsation generator 100. The driving control unit 600 controls the channel switching valve 26 to supply the fluid from the pump 700 to the hand piece 30 through both of the first channel and the second channel and drives, in cooperation with the ejection of the fluid by the pump 700, the respective piezoelectric elements 401 of the first to fifth pulsation generators 100a to 100e to eject the fluid from the first to fifth pulsation generators 100a to 100e in a pulse-like manner. Consequently, the air bubbles remaining in the connection tubes 25 and the pulsation generators 100 are discharged from the distal-end opening sections 211 of the pulsation generators 100. The degassing processing is performed until a predetermined time elapses (or the slider 720 moves a predetermined distance) or until the operator operates the flushing switch 628 to input an OFF signal.

Note that the predetermined speed, the predetermined time, or the predetermined distance for moving the slider 720 in the degassing processing is stored in the driving control unit 600 and the pump control unit 710 beforehand.

In this way, the preparation operation (the preliminary pressurization, the priming processing, and the degassing processing) is completed.

When the preparation operation ends, the pump control unit 710 closes the pinch valve 750 and detects the pressure of the fluid stored in the fluid storing unit 765 of the fluid container 760. The pump control unit 710 performs control for adjusting the position of the slider 720 such that the pressure falls within the rough window.

Thereafter, if the pressure of the fluid in the fluid storing unit 765 is within the rough window, the fluid can be ejected from the pulsation generator 100 in a pulse-like manner.

In this state, when the pulsation-generating-unit start switch 625 is operated by the foot of the surgeon and an ON signal of the pulsation-generating-unit start switch 625 is input to the driving control unit 600, the driving control unit 600 switches the channel switching valve 26 such that the fluid is supplied to the pulsation generator 100 used in the mode (the mode A, the mode B, or the mode C) selected by the pulsation-generating-unit changeover switch 629. According to a signal transmitted from the driving control unit 600, the pump control unit 710 opens the pinch valve 750, moves the slider 720 in the push-in direction at predetermined speed at timing simultaneous or substantially simultaneous with the opening of the pinch valve 750 (e.g., with a time difference of several milliseconds to several tens milliseconds), and starts the supply of the fluid to the pulsation generator 100.

In this case, the speed of the movement of the slider 720 by the pump control unit 710 (a fluid supply amount per a predetermined time) is different according to the mode selected by the pulsation-generating-unit changeover switch 629. The moving speed of the slider 720 at the time when the mode A (an incision mode) is first speed (a first supply amount (a first predetermined amount) per the predetermined time). The moving speed of the slider 720 at the time when the mode B (a crushing mode) is selected is second speed (a second supply amount (a second predetermined amount) per the predetermined time). The moving speed of the slider 720 at the time when the mode C (a crushing mode) is selected is third speed (a third supply amount (a second predetermined amount) per the predetermined time).

The driving control unit 600 starts the driving of the piezoelectric element 401 in the pulsation generator 100 used in the mode selected by the pulsation-generating-unit changeover switch 629 and changes the volume of the fluid chamber 501 to generate a pulsed flow. In this way, the fluid is ejected in a pulse-like manner at high speed from the distal-end opening section 211 at the distal end of the pulsation generator 100.

Thereafter, when the surgeon operates the pulsation-generating-unit start switch 625 by foot and an OFF signal of the pulsation-generating-unit start switch 625 is input to the driving control unit 600, the driving control unit 600 stops the driving of the piezoelectric element 401. According to a signal transmitted from the driving control unit 600, the pump control unit 710 stops the movement of the slider 720 and closes the pinch valve 750. In this way, the ejecting of the fluid from the pulsation generator 100 stops.

Note that, the pump 700 according to this embodiment has the configuration in which the slider 720 presses the fluid container 760 configured as the injection cylinder including the syringe 761 and the plunger 762. However, the pump 700 may have a configuration shown in FIG. 3.

Figure 3:
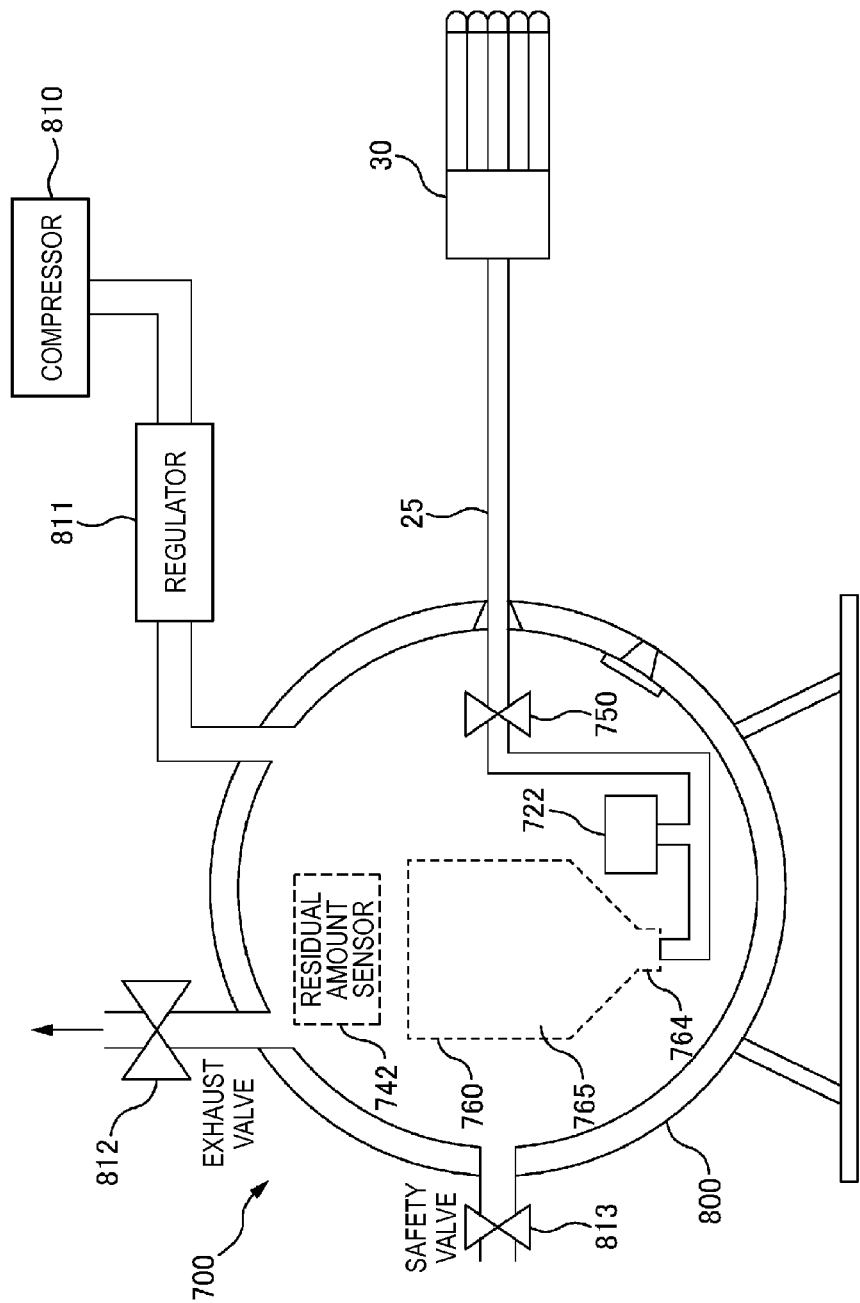
FIG. 3 is a block diagram showing the configuration of the pump according to the embodiment of the invention.

The pump 700 shown in FIG. 3 has a configuration in which the fluid container 760 configured as an infusion fluid bag, which stores the fluid, is attached in a pressurization chamber 800 and, after the air supplied from a compressor 810 is smoothed by a regulator 811, the air is pressure-fed into the pressurization chamber 800 to press the fluid container 760.

In a state in which the air in the pressurization chamber 800 is pressurized to press the fluid container 760, when the pinch valve 750 is opened, the fluid stored in the fluid storing unit 765 of the fluid container 760 flows out from the opening section 764 and is supplied to the pulsation generator 100 through the connection tube 25.

Note that the air in the pressurization chamber 800 is emitted to the atmosphere by opening an exhaust valve 812. When the pressure of the air in the pressurization chamber 800 exceeds predetermined pressure, even if the exhaust valve 812 is not opened, the air in the pressurization chamber 800 is emitted to the atmosphere when a safety valve 813 opens.

Note that, although not shown in FIG. 3, the compressor 810, the regulator 811, the exhaust valve 812, and the pinch valve 750 are controlled by the pump control unit 710.

Detection signals output from the pressure sensor 722 that detects the pressure of the fluid in the fluid container 760 and the residual amount sensor 742 that detects the residual amount of the fluid in the fluid container 760 are also input to the pump control unit 710.

In the case of the pump 700 shown in FIG. 3, the compressor 810, the regulator 811, and the pressurization chamber 800 configure the fluid pressing unit 731.

By adopting the pump 700 having such a form, it is possible to increase an amount of the fluid that can be supplied to the pulsation generator 100 per unit time. It is also possible to supply the fluid at high pressure with the pulsation generator 100. Further, since the infusion fluid bag, which stores the fluid, is directly used as the fluid container 760, it is possible to prevent contamination of the fluid. It is also possible to continuously feed the fluid to the pulsation generator 100 without causing pulsation.

Besides, in this embodiment, the driving control unit 600 is disposed in a position separated from the pump 700 and the pulsation generator 100. However, the driving control unit 600 may be configured integrally with the pump 700.

When a surgical operation is performed using the fluid ejecting device 1, a part griped by the surgeon is the hand piece 30. Therefore, the connection tube 25 to the hand piece 30 is desirably as flexible as possible. It is desirable that the connection tube 25 is a flexible and thin tube and the ejection pressure of the fluid from the pump 700 is set to low pressure in a range in which the fluid can be fed to the hand piece 30. Therefore, the ejection pressure of the pump 700 is set to approximately 0.3 atm (0.03 MPa) or less.

In particular, when there is a risk that a failure of an apparatus causes a serious accident as in brain surgery, spouting of high-pressure fluid in cutting or the like of the connection tube 25 has to be avoided. Therefore, it is also requested to keep the ejection pressure from the pump 700 at low pressure.

Pulsation Generator

The structure of the pulsation generator 100 according to this embodiment is explained.

Figure 4:
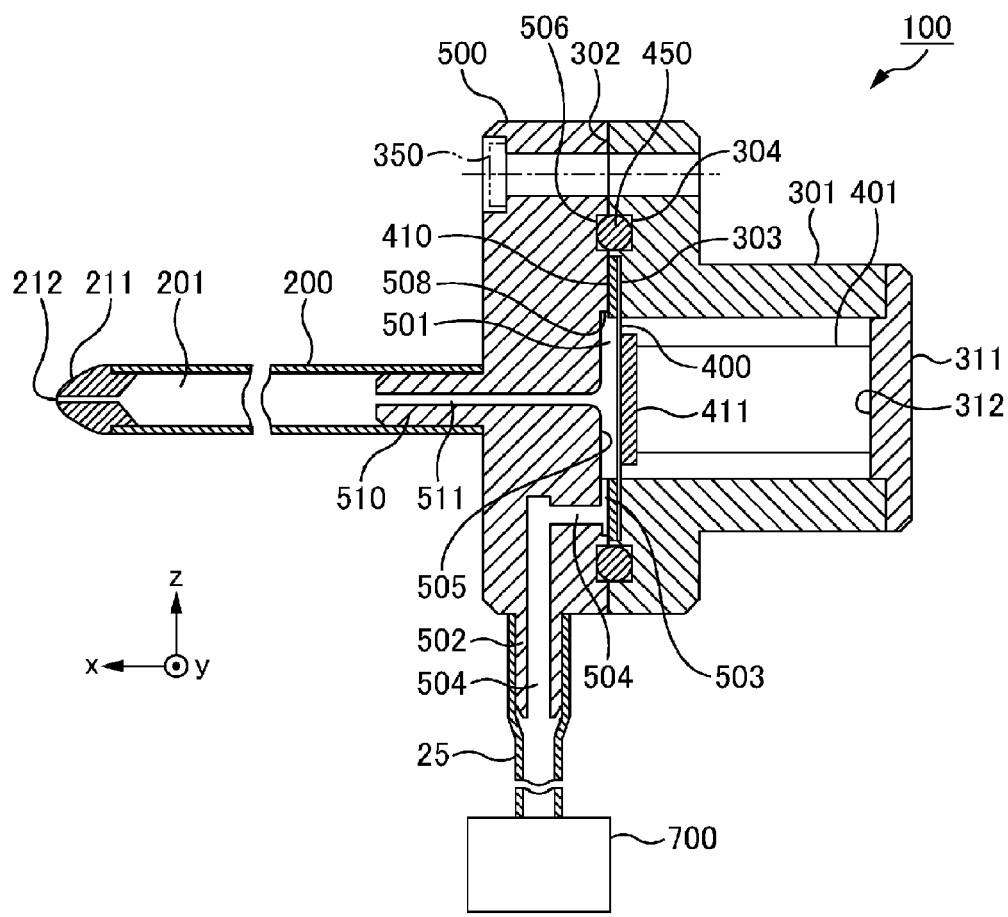
FIG. 4 is a sectional view showing the structure of a pulsation generator according to the embodiment of the invention.

FIG. 4 is a sectional view showing the structure of the pulsation generator 100 according to this embodiment. In FIG. 4, the fluid ejecting pipe 200 including a pulsation generating unit configured to generating pulsation of the fluid and including a connection channel 201 functioning as a channel for ejecting the fluid is connected to the pulsation generator 100.

In the pulsation generator 100, an upper case 500 and a lower case 301 are respectively joined on surfaces opposed to each other. The upper case 500 and the lower case 301 are screwed by four fixing screws 350 (not shown in the figure). The lower case 301 is a cylindrical member having a brim section. One end portion of the lower case 301 is closed by a bottom plate 311. The piezoelectric element 401 is disposed in the inner space of the lower case 301.

The piezoelectric element 401 is a stacked piezoelectric element and configures an actuator. One end portion of the piezoelectric element 401 is fixedly attached to the diaphragm 400 via a top plate 411. The other end portion of the piezoelectric element 401 is fixedly attached to an upper surface 312 of the bottom plate 311.

The diaphragm 400 is made of a disk-like metal thin plate. In a recessed section 303 of the lower case 301, a circumferential edge portion of the diaphragm 400 is closely attached and fixedly attached to the bottom surface of a recessed section 303. By inputting a drive signal to the piezoelectric element 401 functioning as a volume changing unit, the volume of the fluid chamber 501 is changed via the diaphragm 400 according to expansion and contraction of the piezoelectric element 401.

On the upper surface of the diaphragm 400, a reinforcing plate 410 made of a disk-like metal thin plate having an opening section in the center is stacked and disposed.

In the upper case 500, a recessed section is formed in the center of the surface opposed to the lower case 301. A rotating body shape configured from the recessed section and the diaphragm 400 and filled with the fluid is the fluid chamber 501. That is, the fluid chamber 501 is a space surrounded by a sealing surface 505 and an inner circumferential sidewall 508 of the recessed section of the upper case 500 and the diaphragm 400. An outlet channel 511 is drilled in substantially the center of the fluid chamber 501.

The outlet channel 511 is pierced from the fluid chamber 501 to an end portion of an outlet cannel pipe 510 projected from one end face of the upper case 500. A connecting section of the outlet channel 511 to the sealing surface 505 of the fluid chamber 501 is smoothly rounded in order to reduce fluid resistance.

Note that, in this embodiment (see FIG. 4), the shape of the fluid chamber 501 explained above is a substantially cylindrical shape sealed at both ends. However, the shape may be a conical shape or a trapezoidal shape or may be a semispherical shape or the like inside view and is not limited to the cylindrical shape. For example, if the connecting section of the outlet channel 511 and the sealing surface 505 is formed in a shape like a funnel, it is easy to discharge air bubbles in the fluid chamber 501 explained below.

The fluid ejecting pipe 200 is connected to the outlet channel pipe 510. The connection channel 201 is drilled in the fluid ejecting pipe 200. The diameter of the connection channel 201 is larger than the diameter of the outlet channel 511. The thickness of a pipe section of the fluid ejecting pipe 200 is set in a range in which the pipe section has rigidity for not absorbing pressure pulsation of the fluid.

The distal-end opening section 211 is inserted into the distal end portion of the fluid ejecting pipe 200. The fluid-ejecting opening section (an ejection port) 212 is drilled in the distal-end opening section 211. The diameter of the fluid-ejecting opening section 212 is smaller than the diameter of the connection channel 201.

On the side surface of the upper case 500, an inlet channel pipe (a fluid intake port) 502, into which the connection tube 25 for supplying the fluid from the pump 700 is inserted, is projected. A connection channel 504 on an inlet channel side is drilled in the inlet channel pipe 502. The connection channel 504 communicates with an inlet channel 503. The inlet channel 503 is formed in a groove shape in the circumferential edge portion of the sealing surface 505 of the fluid chamber 501 and communicates with the fluid chamber 501.

On the joining surface of the upper case 500 and the lower case 301, in a separated position in the outer circumferential direction of the diaphragm 400, a packing box 304 is formed on the lower case 301 side and a packing box 506 is formed on the upper case 500 side. A ring-like packing 450 is attached in a space formed by the packing boxes 304 and 506.

When the upper case 500 and the lower case 301 are assembled, the circumferential edge portion of the diaphragm 400 and the circumferential edge portion of the reinforcing plate 410 are closely set in contact with the circumferential edge portion of the sealing surface 505 of the upper case 500 by the bottom surface of the recessed section 303 of the lower case 301. In this case, the packing 450 is pressed by the upper case 500 and the lower case 301 to prevent a fluid leak from the fluid chamber 501.

When the fluid is ejected, the inside of the fluid chamber 501 is in a high pressure state of 30 atm (3 MPa) or higher. It is likely that the fluid slightly leaks in joining sections of the diaphragm 400, the reinforcing plate 410, the upper case 500, and the lower case 301. However, the leak is prevented by the packing 450.

When the packing 450 is disposed as shown in FIG. 4, the packing 450 is compressed by the pressure of the fluid leaking from the fluid chamber 501 at high pressure. The packing 450 is more strongly pressed against the walls in the packing boxes 304 and 506. Therefore, it is possible to more surely prevent the leak of the fluid. Consequently, it is possible to maintain a high pressure rise in the fluid chamber 501 during driving.

Figure 5:
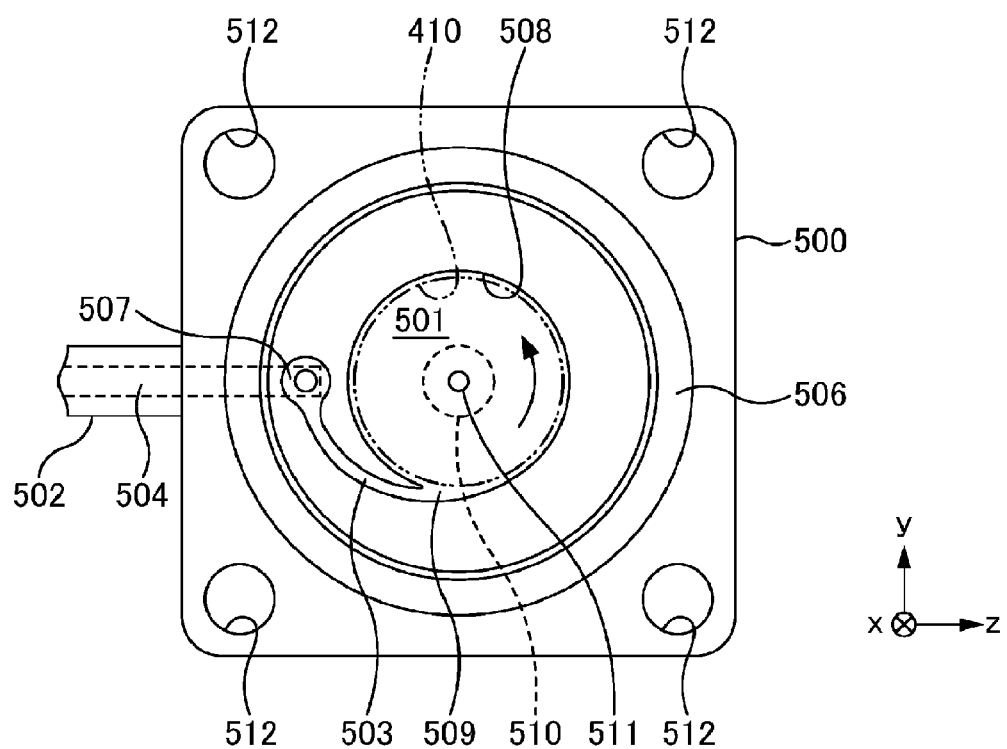
FIG. 5 is a plan view showing a form of an inlet channel according to the embodiment of the invention.

The inlet channel 503 formed in the upper case 500 is explained more in detail with reference to FIG. 5.

FIG. 5 is a plan view showing a form of the inlet channel 503. A state in which the upper case 500 is viewed from the joining surface side with the lower case 301 is shown.

In FIG. 5, the inlet channel 503 is formed in a circumferential edge groove shape of the sealing surface 505 of the upper case 500.

One end portion of the inlet channel 503 communicates with the fluid chamber 501. The other end portion of the inlet channel 503 communicates with the connection channel 504. A fluid reservoir 507 is formed in a connecting section of the inlet channel 503 and the connection channel 504. A connecting section of the fluid reservoir 507 and the inlet channel 503 is smoothly rounded to reduce fluid resistance.

The inlet channel 503 communicates with the inner circumferential sidewall 508 of the fluid chamber 501 toward a substantially tangential direction. The fluid supplied from the pump 700 (see FIG. 1) at predetermined pressure flows along the inner circumferential sidewall 508 (in a direction indicated by an arrow in FIG. 5) to generate a swirl flow in the fluid chamber 501. The swirl flow is pressed to the inner circumferential sidewall 508 side with a centrifugal force by swirling. The air bubbles included in the fluid chamber 501 concentrate on the center of the swirl flow.

The air bubbles collected in the center are removed from the outlet channel 511. Therefore, it is more desirable to provide the outlet channel 511 in the vicinity of the center of the swirl flow, that is, in the axial center of a rotating body shape.

As shown in FIG. 5, the inlet channel 503 is curved. The inlet channel 503 may communicate with the fluid chamber 501 along a straight line without being curved. However, the inlet channel 503 is curved to increase channel length and obtain desired inertance (explained below) in a narrow space.

Note that, as shown in FIG. 5, the reinforcing plate 410 is disposed between the diaphragm 400 and the circumferential edge portion of the sealing surface 505 in which the inlet channel 503 is formed. The reinforcing plate 410 is provided to improve durability of the diaphragm 400. A cutout-like connection opening section 509 is formed in a connecting section of the inlet channel 503 to the fluid chamber 501. Therefore, when the diaphragm 400 is driven at a high frequency, it is likely that stress concentration occurs in the vicinity of the connection opening section 509 to cause fatigue fracture. Therefore, the reinforcing plate 410 having a continuous opening section without a cutout section is disposed to prevent stress concentration from occurring in the diaphragm 400.

In the outer circumferential corner portions of the upper case 500, screw holes 512 are opened in four places. The upper case 500 and the lower case 301 are screwed and joined in the positions of the screw holes.

Note that, although not shown in the figure, the reinforcing plate 410 and the diaphragm 400 can be joined and integrally stacked and fixedly attached. A method of fixedly attaching the reinforcing plate 410 and the diaphragm 400 may be a method of sticking the reinforcing plate 410 and the diaphragm 400 using an adhesive or may be a method such as solid phase diffusion joining or welding. However, the reinforcing plate 410 and the diaphragm 400 are more desirably closely attached on a joining surface.

Operation of the Pulsation Generator

The operation of the pulsation generator 100 in this embodiment is explained with reference to FIGS. 1 to 5. Fluid ejection by the pulsation generator 100 in this embodiment is performed by a difference between inertance L1 (sometimes referred to as combined inertance L1) on the inlet channel 503 side and inertance L2 (sometimes referred to as combined inertance L2) on the outlet channel 511 side.
Inertance
First, the inertance is explained.
When the density of the fluid is represented as ρ, the sectional area of a channel is represented as S, and the length of the channel is represented as h, inertance L is represented by L=ρ×h/S. When a pressure difference of the channel is represented as ΔP and a flow rate of the fluid flowing through the channel is represented as Q, by transforming an equation of motion in the channel using the inertance L, a relation of ΔP=L×dQ/dt is derived.

That is, the inertance L indicates a degree of influence on a temporal change of the flow rate. The temporal change of the flow rate is smaller as the inertance L is larger. The temporal change of the flow rate is larger as the inertance L is smaller.

Combined inertance concerning parallel connection of a plurality of channels and series connection of a plurality of channels having different shapes can be calculated by combining inertances of respective channels in the same manner as parallel connection or series connection of inductances in an electric circuit.

Note that, since the diameter of the connection channel 504 is set sufficiently large with respect to the diameter of the inlet channel 503, the inertance L1 on the inlet channel 503 side is calculated in a range of the inlet channel 503. In this case, since the connection tube 25 that connects the pump 700 and the inlet channel 503 has flexibility, the connection tube 25 may be excluded from the calculation of the inertance L1.

Since the diameter of the connection channel 201 is far larger than the diameter of the outlet channel 511 and the thickness of the pipe section (the pipe wall) of the fluid ejecting pipe 200 is small, the influence of the diameter of the connection channel 201 and the thickness of the pipe section of the fluid ejecting pipe 200 on the inertance L2 is very small. Therefore, the inertance L2 on the outlet channel 511 side may be replaced with the inertance of the outlet channel 511.

Note that the pipe wall of the fluid ejecting pipe 200 has sufficient rigidity for pressure propagation of the fluid.

In this embodiment, the channel length and the sectional area of the inlet channel 503 and the channel length and the sectional area of the outlet channel 511 are set such that the inertance L1 on the inlet channel 503 side is larger than the inertance L2 on the outlet channel 511 side.

Ejecting of the Fluid

The operation of the pulsation generator 100 is explained below.

The fluid is supplied to the inlet channel 503 by the pump 700 at given pressure. As a result, when the piezoelectric element 401 does not perform an operation, the fluid flows in the fluid channel 501 with a difference between an ejection force of the pump 700 and a fluid resistance value of the entire inlet channel 503 side.

When a drive signal is input to the piezoelectric element 401 and the piezoelectric element 401 suddenly expands, the pressure in the fluid chamber 501 quickly rises and reaches several tens atm if the inertances L1 and L2 on the inlet channel 503 side and the outlet channel 511 side have sufficient magnitude.

The pressure in the fluid chamber 501 is far larger than the pressure by the pump 700 applied to the inlet channel 503. Therefore, inflow of the fluid into the fluid chamber 501 from the inlet channel 503 side decreases and outflow from the outlet channel 511 increases because of the pressure.

Since the inertance L1 of the inlet channel 503 is larger than the inertance L2 of the outlet channel 511, an increase amount of the fluid ejected from the outlet channel 511 is larger than a decrease amount of the flow rate of the fluid flowing into the fluid chamber 501 from the inlet channel 503. Therefore, pulse-like fluid ejection, that is, a pulsed flow occurs in the connection channel 201. Pressure fluctuation in the ejection propagates through the fluid ejecting pipe 200. The fluid is ejected from the fluid-ejecting opening section 212 of the distal-end opening portion 211 at the distal end.

Since the diameter of the fluid-ejecting opening section 212 of the distal-end opening portion 211 is smaller than the diameter of the outlet channel 511, the fluid is ejected as pulse-like droplets at higher pressure and higher speed.

On the other hand, the inside of the fluid chamber 501 changes to a decompressed state immediately after a pressure rise because of interaction of a decrease in a fluid inflow amount from the inlet channel 503 and an increase in a fluid outflow from the outlet channel 511. As a result, a flow of the fluid in the inlet channel 503 flowing to the fluid chamber 501 at speed same as the speed before the operation of the piezoelectric element 401 is restored after the elapse of a predetermined time by both of the pressure of the pump 700 and the decompressed state in the fluid chamber 501.

After the flow of the fluid in the inlet channel 503 is restored, if the piezoelectric element 401 expands, it is possible to continuously eject the pulsed flow from the distal-end opening section 211.

Removal of the Air Bubbles

A removing operation for the air bubbles in the fluid chamber 501 is explained.

As explained above, the inlet channel 503 communicates with the fluid chamber 501 through the route approaching the fluid chamber 501 while turning around the fluid chamber 501. The outlet channel 511 is opened in the vicinity of the rotation axis of the substantial rotating body shape of the fluid chamber 501.

Therefore, the fluid flowing into the fluid chamber 501 from the inlet channel 503 swirls along the inner circumferential sidewall 508 in the fluid chamber 501. The fluid is pressed to the inner circumferential sidewall 508 side of the fluid chamber 501 by a centrifugal force. Air bubbles included in the fluid concentrate on the center of the fluid chamber 501. As a result, the air bubbles are discharged from the outlet channel 511.

Therefore, even in a very small volume change of the fluid chamber 501 due to the piezoelectric element 401, the pressure fluctuation is not hindered by the air bubbles and a sufficient pressure rise is obtained.

According to this embodiment, since the fluid is supplied to the inlet channel 503 by the pump 700 at predetermined pressure, the fluid is supplied to the inlet channel 503 and the fluid chamber 501 even in a state in which the driving of the pulsation generator 100 is stopped. Therefore, it is possible to start an initial operation even if a priming water operation is not performed.

Since the fluid is ejected from the fluid-ejecting opening section 212 further reduced than the diameter of the outlet channel 511, fluid pressure is higher than the fluid pressure in the outlet channel 511. Therefore, it is possible eject the fluid at high speed.

Further, the fluid ejecting pipe 200 has rigidity enough for transmitting the pulsation of the fluid fed from the fluid chamber 501 to the fluid-ejecting opening section 212. Therefore, there is an effect that it is possible to eject a desired pulsed flow without hindering pressure propagation of the fluid from the pulsation generator 100.

Since the inertance of the inlet channel 503 is set larger than the inertance of the outlet channel 511, an increase in an outflow amount larger than a decrease in an inflow amount of the fluid to the fluid chamber 501 from the inlet channel 503 occurs in the outlet channel 511. Pulse-like fluid ejection into the fluid ejecting pipe 200 can be performed. Therefore, there is an effect that a check valve does not have to be provided on the inlet channel 503 side, the structure of the pulsation generator 100 can be simplified, cleaning of the inside is easy, and a concern about durability due to the use of the check valve can be eliminated.

Note that, if the volume of the fluid chamber 501 is suddenly reduced by setting the inertances of both of the inlet channel 503 and the outlet channel 511 sufficiently large, it is possible to suddenly increase the pressure in the fluid chamber 501.

By generating pulsation using the piezoelectric element 401 functioning as the volume changing unit and the diaphragm 400, it is possible to realize simplification of the structure of the pulsation generator 100 and a reduction in size involved in the simplification. A maximum frequency of a volume change of the fluid chamber 501 can be set to a high frequency equal to or higher than 1 KHz. This is optimum for ejecting of a high-speed pulsed flow.

The pulsation generator 100 generates a swirl flow in the fluid in the fluid chamber 501 with the inlet channel 503. Therefore, the pulsation generator 100 can push the fluid in the fluid chamber 501 in the outer circumferential direction of the fluid chamber 501 with a centrifugal force, concentrate the air bubbles included in the fluid on the center of the swirl flow, that is, in the vicinity of the axis of the substantial rotating body shape, and remove the air bubbles from the outlet channel 511 provided in the vicinity of the axis of the substantial rotating body shape. Consequently, it is possible to prevent a decrease in pressure amplitude due to the air bubbles held up in the fluid chamber 501 and continue stable driving of the pulsation generator 100.

Further, the inlet channel 503 is formed to communicate with the fluid chamber 501 through the route approaching the fluid chamber 501 while turning around the fluid chamber 501. Therefore, it is possible to generate the swirl flow without using a dedicated structure for swirling the fluid on the inside of the fluid chamber 501.

The groove-shaped inlet channel 503 is formed at the outer circumferential edge portion of the sealing surface 505 of the fluid chamber 501. Therefore, it is possible to form the inlet chamber 503 functioning as the swirl-flow generating unit without increasing the number of components.

Since the reinforcing plate 410 is provided on the upper surface of the diaphragm 400, the diaphragm 400 is driven with the opening section outer circumference of the reinforcing plate 410 as a fulcrum. Therefore, stress concentration less easily occurs. It is possible to improve the durability of the diaphragm 400.

Note that, if the corners of the joining surface of the reinforcing plate 410 to the diaphragm 400 are rounded, it is possible to further reduce the stress concentration of the diaphragm 400.

If the reinforcing plate 410 and the diaphragm 400 are stacked and integrally fixedly attached, it is possible to improve assemblability of the pulsation generator 100. Further, there is also a reinforcing effect of the outer circumferential edge portion of the diaphragm 400.

The fluid reservoir 507 for holding up the fluid is provided in the connecting section of the connection channel 504 and the inlet channel 503 on the inlet side to which the fluid is supplied from the pump 700. Therefore, it is possible to suppress the influence of the inertance of the connection channel 504 on the inlet channel 503.

Further, on the joining surface of the upper case 500 and the lower case 301, the ring-like packing 450 is provided in the position spaced apart in the outer circumferential direction of the diaphragm 400. Therefore, it is possible to prevent a leak of the fluid from the fluid chamber 501 and prevent a pressure drop in the fluid chamber 501.

Ejecting Modes

As explained above, the fluid ejection device 1 according to this embodiment can select the mode (the mode A, the mode B, or the mode C) with the pulsation-generating-unit changeover switch 629. The surgeon selects the mode A (the incision mode) when incising a biological tissue and selects the mode B (the crushing mode) or the mode C (the crushing mode) when crushing the biological tissue.

If the mode A is selected, the fluid ejection device 1 ejects the fluid using the first nozzle unit. If the mode B or the mode C is selected, the fluid ejection device 1 ejects the fluid using the second nozzle unit.

The first nozzle unit is a nozzle including at least one of the plurality of pulsation generators 100. In this embodiment, the first pulsation generator 100a corresponds to the first nozzle unit. The second nozzle unit is a nozzle including at least one of the plurality of pulsation generators 100. In this embodiment, if the mode B is selected, the first to fifth pulsation generators 100a to 100e correspond to the second nozzle unit. If the mode C is selected, the second to fifth pulsation generators 100b to 100e correspond to the second nozzle unit.

In the fluid ejection device 1 according to this embodiment, a total area of cross sections of ejection ports of the second nozzle unit that ejects the fluid when the mode B or the mode C is selected is set larger than a total area of cross sections of ejection ports of the first nozzle unit that ejects the fluid when the mode A is selected. A state of the setting of the total areas is shown in FIG. 6.

In FIG. 6, black circles and white circles indicate cross sections of the fluid-ejecting opening sections 212 drilled in the distal-end opening portions 211 attached to the distal ends of the pulsation generators 100. The white circles indicate that the fluid is not ejected. The black circles indicate that the fluid is ejected.

As shown in FIG. 6, a total area SA of the cross sections of the ejection ports of the first nozzle unit that ejects the fluid when the mode A is selected is across sectional area S1 of a first fluid-ejecting opening section 212a.

A total area SB of the cross sections of the ejection ports of the second nozzle unit that ejects the fluid when the mode B is selected is a sum of cross sectional areas S1+S2+S3+S4+S5 of the first fluid-ejecting opening section 212a to a fifth fluid-ejecting opening section 212e.

Similarly, a total area SC of the cross sections of the ejection ports of the second nozzle unit that ejects the fluid when the mode C is selected is a sum of cross sectional areas S2+S3+S4+S5 of a second fluid-ejecting opening section 212b to the fifth fluid-ejecting opening section 212e.

SB and SC are set larger than SA.

In this way, in the fluid ejection device 1 according to this embodiment, when a biological tissue is crushed, the fluid is ejected from the ejection port having a larger area. Therefore, it is possible to more efficiently perform the crushing of the biological tissue.

As in the mode B, in the crushing of the biological tissue, when all of the first to fifth pulsation generators 100a to 100e are used, it is possible to eject the fluid from the ejection ports having a still larger area. Therefore, it is possible to effectively perform the crushing of the biological tissue.

As in the mode C, in the crushing of the biological tissue, when the first pulsation generator 100*a* used for the incision of the biological tissue is not used, as the first pulsation generator 100*a*, a pulsation generator having a function, a structure, and a shape suitable for the incision of the biological tissue can be used. Similarly, as the second to fifth pulsation generators 100*b* to 100*e*, a pulsation generator having a function, a structure, and a shape suitable for the crushing of the biological tissue can be used. For example, the sectional areas of the fluid-ejecting opening sections 212, the lengths of the fluid ejecting pipes 200, and the like can be respectively optimized for the incision and the crushing.

If the incision mode (the mode A) is selected, the pump 700 according to this embodiment supplies a first predetermined amount of the fluid to the hand piece 30 per a predetermined time. If the crushing mode (the mode B or the mode C) is selected, the pump 700 supplies a second predetermined amount of the fluid to the hand piece 30 per the predetermined time.

The first predetermined amount is a supply amount of the fluid per the predetermined time supplied when the incision mode is selected. The second predetermined amount is a supply amount of the fluid per the predetermined time supplied when the crushing mode is selected.

Therefore, if the mode A (the incision mode) is selected, a first supply amount (the first predetermined amount) of the fluid is supplied to the hand piece 30 per the predetermined time. If the mode B (the crushing mode) is selected, a second supply amount (the second predetermined amount) of the fluid is supplied to the hand piece 30 per the predetermined time. If the mode C (the crushing mode) is selected, a third supply amount (the second predetermined amount) of the fluid is supplied to the hand piece 30 per the predetermined time.

Specifically, if the mode A is selected, the pump 700 controls the slider 720 to supply the first supply amount, which is an amount of the fluid ejected from the first pulsation generator 100*a* in the predetermined time, to the hand piece 30 in the predetermined time.

If the mode B is selected, the pump 700 controls the slider 720 to supply the second supply amount, which is an amount of the fluid ejected from the first to fifth pulsation generators 100*a* to 100*e* in the predetermined time, to the hand piece 30 in the predetermined time. In this case, the second supply amount per the predetermined time is larger than the first supply amount.

If the mode C is selected, the pump 700 controls the slider 720 to supply the third supply amount, which is an amount of the fluid ejected from the second to fifth pulsation generators 100*b* to 100*e* in the predetermined time, to the hand piece 30 in the predetermined time. In this case, the third supply amount is larger than the first supply amount.

Consequently, irrespective of which of the modes is selected, the fluid ejection device 1 according to this embodiment can eject an appropriate amount of the fluid from the pulsation generators 100.

If the incision mode (the mode A) is selected, the fluid ejection device 1 according to this embodiment ejects the fluid from the first nozzle at first ejecting strength. If the crushing mode (the mode B or the mode C) is selected, the fluid ejection device 1 ejects the fluid from the second nozzle at second ejecting strength.

The first ejecting strength is ejecting strength adopted when the incision mode is selected. The second ejecting strength is ejecting strength adopted when the crushing mode is selected.

As explained above, the driving control unit 600 is capable of controlling the ejecting strength by increasing or reducing the voltage or the frequency of the drive signal for driving the piezoelectric element 401.

Consequently, even when the appropriate ejecting strengths are different when the biological tissue is incised and when the biological tissue is crushed, it is possible to eject the fluid at the ejecting strength appropriate for both the incision and the crushing. For example, in most cases, more energy is necessary when the biological tissue is crushed than when the biological tissue is incised. Therefore, it is desirable to set the second ejecting strength higher than the first ejecting strength.

Note that, as explained above, the fluid ejection device 1 according to this embodiment includes the ejecting-strength changeover switch 627. The surgeon can also increase and reduce the ejecting strength of the fluid by operating the ejecting-strength changeover switch 627.

Therefore, the fluid ejection device 1 according to this embodiment is capable of ejecting the fluid at appropriate ejecting strength corresponding to the hardness, viscosity, or the like of a biological tissue that is about to be incised or crushed. Therefore, it is possible to more quickly and safely perform a surgical operation.

Arrangement of the Pulsation Generators 100

As explained above, the hand piece 30 according to this embodiment includes the plurality of pulsation generators 100. However, when a biological tissue is incised, the hand piece 30 ejects the fluid from the first pulsation generator 100*a*.

On the other hand, the surgeon who performs a surgical operation using the hand piece 30 has to clearly recognize, in order to incise the biological tissue in an accurate position, from which pulsation generator 100 among the plurality of pulsation generators 100 the fluid is ejected.

Therefore, in the fluid ejection device 1 according to this embodiment, the hand piece 30 is configured to clearly show the position of the first pulsation generator 100*a* to the surgeon.

Specifically, in the fluid ejection device 1 according to this embodiment, the pulsation generators 100 are arranged such that the position of the distal end in the ejecting direction of the first pulsation generator 100*a* is different from the positions of the distal ends in the ejecting direction of the second to fifth pulsation generators 100*b* to 100*e*.

The arrangement of the pulsation generators 100 is specifically explained below with reference to FIGS. 7 to 11.

Figure 7:
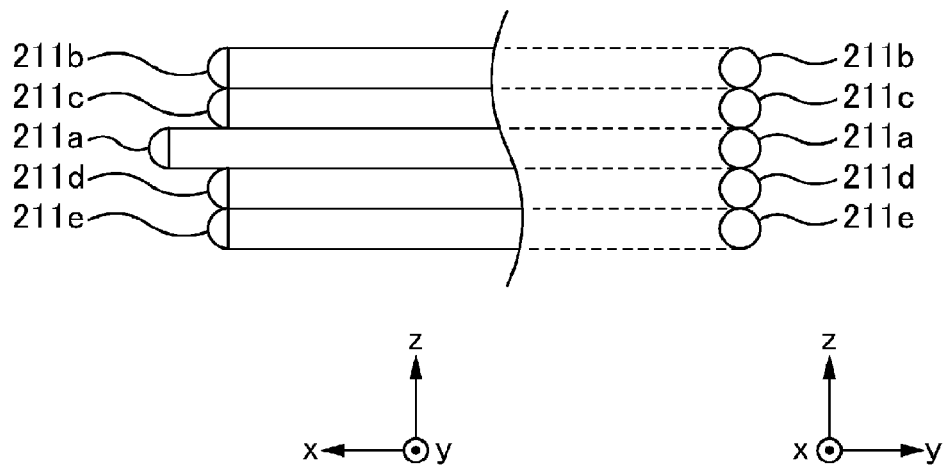
FIG. 7 is a diagram showing an example of the arrangement of a plurality of pulsation generators according to the embodiment of the invention.

FIG. 7 is an example in which the pulsation generators 100 of the hand piece 30 are arranged such that the position of the distal end in the ejecting direction of the first pulsation generator 100*a* further projects in the ejecting direction than the positions of the distal ends in the ejecting direction of the second to fifth pulsation generators 100*b* to 100*e*.

With such a form, the surgeon can clearly recognize the position of the first pulsation generator 100*a*.

In the example shown in FIG. 7, the positions of the distal ends in the ejecting direction of the second to fifth pulsation generators 100*b* to 100*e* are arranged to be aligned with one another. Therefore, it is possible to more easily recognize the position of the distal end in the ejecting direction of the first pulsation generator 100*a*.

In the example shown in FIG. 7, the second to fifth pulsation generators 100*b* to 100*e* are arranged in a row in both directions across the first pulsation generator 100*a*. Therefore, when the fluid is ejected from the second to fifth pulsation generators 100*b* to 100*e* in the crushing mode, it is possible to effectively crush a biological tissue in a wider range.

Note that, in this case, it is desirable that the driving control unit 600 outputs a drive signal such that the ejecting strength of the fluid from the second pulsation generator 100*b* and the fifth pulsation generator 100*e* located at both end portions of the plurality of the pulsation generators 100 is higher than the ejecting strength of the fluid from the third pulsation generator 100*c* and the fourth pulsation generator 100*d*.

By arranging the pulsation generators 100 in this way, it is possible to clarify an outer edge of a crushing range in crushing a biological tissue. Therefore, the surgeon can proceed with crushing work while clearly recognizing a range of the crushing.

Conversely, the driving control unit 600 may output the drive signal such that the ejecting strength of the fluid from the second pulsation generator 100*b* and the fifth pulsation generator 100*e* located at both the end portions of the plurality of pulsation generators 100 is lower than the ejecting strength of the fluid from the third pulsation generator 100*c* and the fourth pulsation generator 100*d*.

In this case, for example, when a place that should be crushed and a place that should not be crushed are close to each other, by reducing ejecting strength of an outer edge portion of a crushing range, it is possible to prevent the latter from being crushed by mistake.

Note that the surgeon may be allowed to freely set strength by providing, in the driving control unit 600, a switch capable of setting whether the ejecting strength of the fluid from the second pulsation generator 100*b* and the fifth pulsation generator 100*e* is set higher or lower than the ejecting strength of the fluid from the third pulsation generator 100*c* and the fourth pulsation generator 100*d* and to which degree the former is set higher or lower than the latter. In this way, it is possible to flexibly adjust the ejecting strength according to various states such as the size and the hardness of a biological tissue to be subjected to a surgical operation and positions of blood vessels. Therefore, it is possible to more effectively perform the surgical operation.

In that case, the ejecting of the fluid from the second pulsation generator 100*b* and the fifth pulsation generator 100*e* can be stopped by the setting of the switch. In this way, it is possible to freely adjust, according to the size of the biological tissue to be crushed, a range in which the fluid is ejected.

Figure 8:
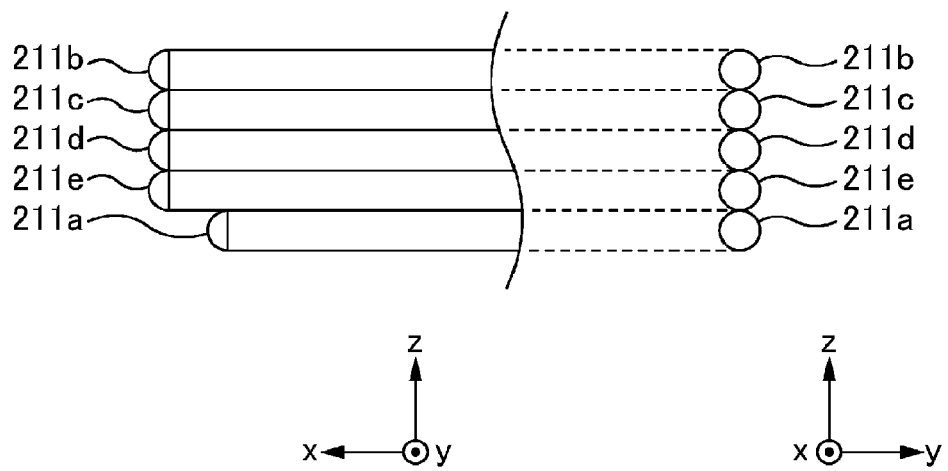
FIG. 8 is a diagram showing an example of the arrangement of the plurality of pulsation generators according to the embodiment of the invention.

FIG. 8 is an example in which the pulsation generators 100 of the hand piece 30 are arranged such that the position of the distal end in the ejecting direction of the first pulsation generator 100*a* further retracts in the ejecting direction than the positions of the distal ends in the ejecting direction of the second to fifth pulsation generators 100*b* to 100*e*.

With such a form as well, the surgeon can clearly recognize the position of the first pulsation generator 100*a*.

In the example shown in FIG. 8 as well, the positions of the distal ends in the ejecting direction of the second to fifth pulsation generators 100*b* to 100*e* are arranged to be aligned with one another. Therefore, it is possible to more easily recognize the position of the distal end in the ejecting direction of the first pulsation generator 100*a*.

Figure 9:
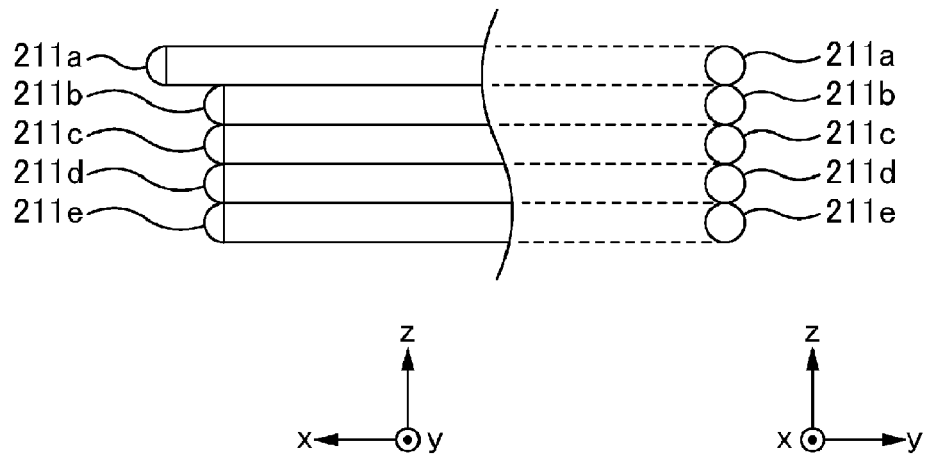
FIG. 9 is a diagram showing an example of the arrangement of the plurality of pulsation generators according to the embodiment of the invention.

FIG. 9 is an example in which, as in FIG. 7, the pulsation generators 100 of the hand piece 30 are arranged such that the position of the distal end in the ejecting direction of the first pulsation generator 100*a* further projects in the ejecting direction than the positions of the distal ends in the ejecting direction of the second to fifth pulsation generators 100*b* to 100*e*.

As in FIG. 7, with such a form, the surgeon can clearly recognize the position of the first pulsation generator 100*a*.

The positions of the distal ends in the ejecting direction of the second to fifth pulsation generators 100*b* to 100*e* are arranged to be aligned with one another. Therefore, it is possible to more easily recognize the position of the distal end in the ejecting direction of the first pulsation generator 100*a*.

Further, in the example shown in FIG. 9, the second to fifth pulsation generators 100*b* to 100*e* are arranged to be aligned in a row on one wide with respect to the first pulsation generator 100*a*. The first pulsation generator 100*a* is arranged at an end portion. Therefore, the surgeon can more clearly recognize the position of the first pulsation generator 100*a*.

Figure 10:
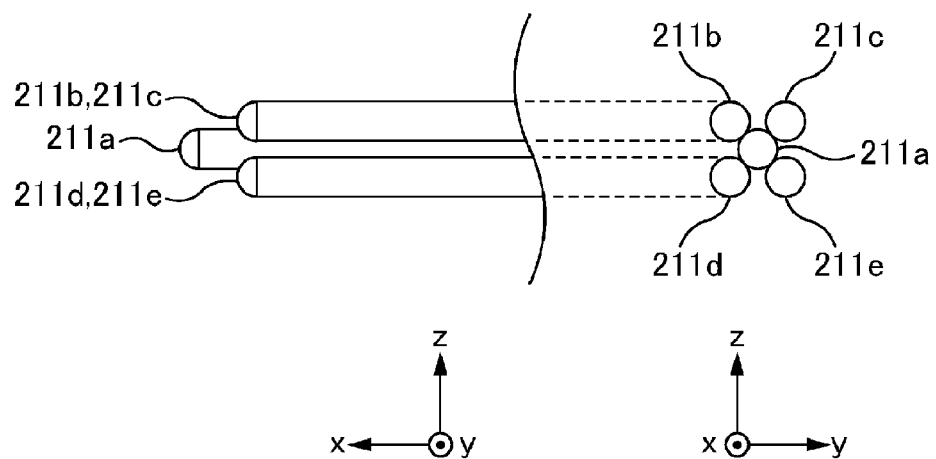
FIG. 10 is a diagram showing an example of the arrangement of the plurality of pulsation generators according to the embodiment of the invention.

FIG. 10 is an example in which, as in FIGS. 7 and 9, the pulsation generators 100 of the hand piece 30 are arranged such that the position of the distal end in the ejecting direction of the first pulsation generator 100*a* further projects in the ejecting direction than the positions of the distal ends in the ejecting direction of the second to fifth pulsation generators 100*b* to 100*e*.

With such a form, the surgeon can clearly recognize the position of the first pulsation generator 100*a*.

The positions of the distal ends in the ejecting direction of the second to fifth pulsation generators 100*b* to 100*e* are aligned with one another. Therefore, it is possible to more easily recognize the position of the distal end in the ejecting direction of the first pulsation generator 100*a*.

In FIG. 10, in particular, the pulsation generators 100 are arranged such that the second to fifth pulsation generators 100*b* to 100*e* surround the first pulsation generator 100*a*.

With such a form, the surgeon can more clearly recognize the position of the first pulsation generator 100*a*.

Further, the first to fifth pulsation generators 100*a* to 100*e* are arranged in a circle centering on and surrounding the first pulsation generator 100*a*. Therefore, it is possible to compactly arrange the first to fifth pulsation generators 100*a* to 100*e*. Therefore, it is possible to reduce the hand piece 30 in size. Further, for example, in a narrow place in the body of a patient, it is possible to bring the distal-end opening sections 211 of the pulsation generators 100 close to a biological tissue and eject the fluid.

Figure 11:
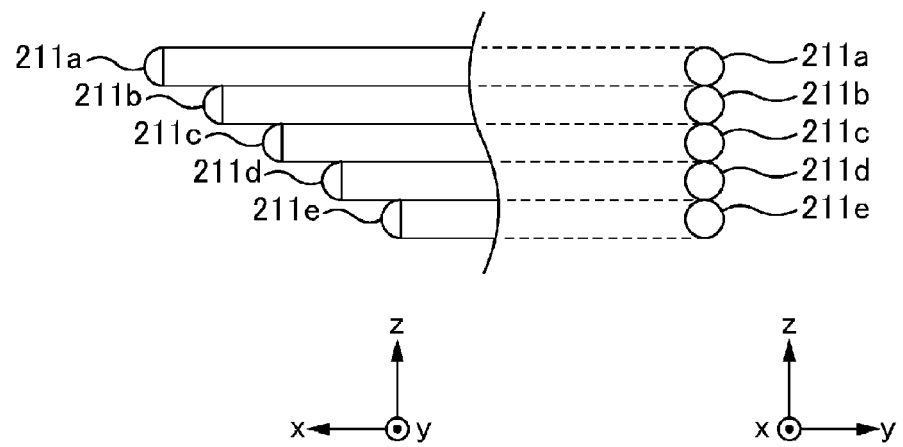
FIG. 11 is a diagram showing an example of the arrangement of the plurality of pulsation generators according to the embodiment of the invention.

FIG. 11 is an example in which, as in FIGS. 7, 9, and 10, the pulsation generators 100 of the hand piece 30 are arranged such that the position of the distal end in the ejecting direction of the first pulsation generator 100*a* further projects in the ejecting direction than the positions of the distal ends in the ejecting direction of the second to fifth pulsation generators 100*b* to 100*e*.

As in FIG. 7, with such a form, the surgeon can clearly recognize the position of the first pulsation generator 100*a*.

In the example shown in FIG. 11, the second to fifth pulsation generators 100*b* to 100*e* are arranged to be aligned in a row on one wide with respect to the first pulsation generator 100*a*. The first pulsation generator 100*a* is arranged at an end portion. Therefore, the surgeon can more clearly recognize the position of the first pulsation generator 100*a*.

Further, in the example shown in FIG. 11, the positions of the respective distal ends in the ejecting direction of the first to fifth pulsation generators 100*a* to 100*e* are arranged such that the positions of the distal ends of the second to fifth pulsation generators 100*b* to 100*e* retract in order of adjacency starting from the first pulsation generator 100a. Therefore, it is possible to more easily recognize the position of the distal end in the ejecting direction of the first pulsation generator 100a. It is also possible to provide the surgeon with a sense of operation closer to a surgical operation performed using a metallic knife.

The fluid ejection device 1 according to this embodiment is explained above. However, with the fluid ejection device 1 according to this embodiment, it is possible to more efficiently perform the crushing of the biological tissue.

For example, when the biological tissue is incised, since the fluid ejection device 1 according to this embodiment can eject the fluid in a straight line from the single pulsation generator 100, it is possible to accurately eject the fluid to a position to be incised. Further, when the biological tissue is crushed, since the fluid can be ejected to a wide range from the plurality of pulsation generators 100, it is possible to efficiently crush the biological tissue to be crushed.

As explained above, with the fluid ejection device 1 according to this embodiment, it is possible to efficiently perform both of the incision and the crushing with one hand piece 30. It is possible to improve an ability for crushing a biological tissue per a unit time.

In the fluid ejection device 1 according to this embodiment, the pulsation generators 100 are arranged to clearly show, when the biological tissue is incised, from which pulsation generator 100 among the plurality of pulsation generators 100 the fluid is ejected. Therefore, the surgeon who performs a surgical operation using the hand piece 30 can incise the biological tissue in a more accurate position.

As explained above, with the fluid ejection device 1 according to this embodiment, it is possible to efficiently carry out the incision and the crushing with one hand piece 30. Even if the hand piece 30 is increased in size because the hand piece 30 includes the plurality of pulsation generators 100, since it is easy to visually recognize the position of the distal end of the first pulsation generator 100a used for incision, the hand piece 30 does not hinder concentration of the surgeon. Further, it is possible to contribute to an efficient surgical operation.

The embodiment is intended to facilitate understanding of the invention and not limitedly interpret the invention. The invention could be modified and improved without departing from the spirit of the invention. Equivalents of the invention are also included in the invention.

What is claimed is:

1. A fluid ejection device comprising:
    a fluid ejection unit including a plurality of nozzles for ejecting fluid and configured to eject the fluid from at least any one of the nozzles in a pulse-like manner according to a drive signal;
    a fluid supplying unit configured to supply the fluid to the fluid ejection unit;
    an ejecting-instruction input unit configured to receive an ejecting instruction input for ejecting the fluid from the fluid ejection unit;
    a mode-selection input unit configured to receive an input of selection information for selecting, when the fluid is ejected from the fluid ejection unit, any one of a first mode for ejecting the fluid using a first nozzle unit including at least one of the plurality of nozzles and a second mode for ejecting the fluid using a second nozzle unit including at least one of the plurality of nozzles; and
    a fluid-ejecting control unit configured to output, when receiving the ejecting instruction input, according to the selection information, the drive signal to the fluid ejection unit such that the fluid is ejected from the first nozzle unit or the second nozzle unit, wherein
    a total area of cross sections of ejection ports of the nozzles belonging to the second nozzle unit is larger than a total area of cross sections of ejection ports of the nozzles belonging to the first nozzle unit.

2. The fluid ejection device according to claim 1, wherein the nozzles belonging to the first nozzle unit also belong to the second nozzle unit.

3. The fluid ejection device according to claim 1, wherein the nozzles belonging to the first nozzle unit do not belong to the second nozzle unit.

4. The fluid ejection device according to claim 1, wherein, when the fluid ejection unit ejects the fluid, if the first mode is selected, the fluid supplying unit supplies a first predetermined amount of the fluid to the fluid ejection unit per a predetermined time and, if the second mode is selected, the fluid supplying unit supplies a second predetermined amount of the fluid to the fluid ejection unit per the predetermined time.

5. The fluid ejection device according to claim 4, wherein the second predetermined amount is larger than the first predetermined amount.

6. The fluid ejection device according to claim 1, wherein, if the first mode is selected, the fluid ejection unit ejects the fluid from the nozzles belonging to the first nozzle unit at first ejecting strength and, if the second mode is selected, the fluid ejection unit ejects the fluid from the nozzles belonging to the second nozzle unit at second ejecting strength.

7. The fluid ejection device according to claim 6, wherein the second ejecting strength is higher than the first ejecting strength.

8. The fluid ejection device according to claim 1, wherein a single nozzle belongs to the first nozzle unit, and the nozzles belonging to the second nozzle unit include all the nozzles other than the nozzle belonging to the first nozzle unit.

* * * * *